(12) United States Patent
Stokes et al.

(10) Patent No.: US 11,090,052 B2
(45) Date of Patent: Aug. 17, 2021

(54) SURGICAL CLIP APPLIER WITH PASSIVE JAW CLOSURE

(71) Applicant: Ethicon LLC, Guaynabo, PR (US)

(72) Inventors: Michael J. Stokes, Cincinnati, OH (US); Gregory G. Scott, Cincinnati, OH (US); Disha Labhasetwar, Cincinnati, OH (US); John Edward Brady, Cincinnati, OH (US)

(73) Assignee: Cilag GmbH International

( * ) Notice: Subject to any disclaimer, the term of this patent is extended or adjusted under 35 U.S.C. 154(b) by 72 days.

(21) Appl. No.: 16/176,435

(22) Filed: Oct. 31, 2018

(65) Prior Publication Data

US 2020/0129178 A1    Apr. 30, 2020

(51) Int. Cl.
| | | |
|---|---|---|
| A61B 17/10 | (2006.01) | |
| A61B 34/37 | (2016.01) | |
| A61B 34/30 | (2016.01) | |
| A61B 17/00 | (2006.01) | |

(52) U.S. Cl.
CPC .............. *A61B 17/10* (2013.01); *A61B 34/37* (2016.02); *A61B 2017/00367* (2013.01); *A61B 2034/305* (2016.02)

(58) Field of Classification Search
CPC ...... A61B 2034/305; A61B 2017/2908; A61B 2017/00327; A61B 2017/00314; A61B 2017/003; A61B 34/30; A61B 17/1285; A61B 17/128; A61B 17/105; A61B 17/083; A61B 17/0682
See application file for complete search history.

(56) References Cited

U.S. PATENT DOCUMENTS

| | | | |
|---|---|---|---|
| 5,340,360 A | 8/1994 | Stefanchik | |
| 5,474,566 A * | 12/1995 | Alesi | A61B 17/1285 606/139 |
| 5,951,574 A | 9/1999 | Stefanchik et al. | |
| 6,824,548 B2 | 11/2004 | Smith et al. | |
| 6,843,794 B2 | 1/2005 | Sixto, Jr. et al. | |
| 7,223,272 B2 | 5/2007 | Francese et al. | |
| 7,615,058 B2 | 11/2009 | Sixto, Jr. et al. | |
| 8,216,257 B2 | 7/2012 | Huitema et al. | |
| 8,328,822 B2 | 12/2012 | Huitema et al. | |
| 8,403,946 B2 * | 3/2013 | Whitfield | A61B 17/1285 606/143 |
| 8,753,356 B2 | 6/2014 | Vitali et al. | |
| 9,364,239 B2 | 6/2016 | Malkowski | |

(Continued)

*Primary Examiner* — George J Ulsh
(74) *Attorney, Agent, or Firm* — Vory, Sater, Seymour and Pease LLP

(57) ABSTRACT

An end effector for a surgical clip applier includes a housing, opposed first and second jaw members extending past a distal end of the housing and each comprising an independent structure movable relative to the other, a first cam track provided on the first jaw member and a second cam track provided on the second jaw member, and a cam providing first and second cam surfaces slidably engageable with the first and second cam tracks, respectively. A biasing device continuously urges the cam in a distal direction relative to the first and second jaw members, wherein the first and second cam surfaces and the first and second cam tracks are angled such that axial movement of the cam in the distal direction relative to the first and second jaw members causes the jaw members to close.

20 Claims, 9 Drawing Sheets

(56) References Cited

U.S. PATENT DOCUMENTS

| | | |
|---|---|---|
| 9,370,400 B2 | 6/2016 | Parihar |
| 9,717,504 B2 | 8/2017 | Huitema |
| 10,039,548 B2 | 8/2018 | Parihar |
| 10,098,689 B2 | 10/2018 | Soni |
| 10,932,792 B2 | 3/2021 | Stokes et al. |
| 2011/0224696 A1 | 9/2011 | Huitema et al. |
| 2015/0127022 A1* | 5/2015 | Whitfield ............... A61B 17/10 606/143 |
| 2016/0213377 A1 | 7/2016 | Shankarsetty |
| 2016/0287252 A1 | 10/2016 | Parihar |

* cited by examiner

SURGICAL CLIP APPLIER WITH PASSIVE JAW CLOSURE

BACKGROUND

Minimally invasive surgical (MIS) tools and procedures are often preferred over traditional open surgical approaches due to their propensity toward reducing post-operative recovery time and leaving minimal scarring. Endoscopic surgery is one type of MIS procedure in which a surgical tool operably connected to an elongate shaft is introduced into the body of a patient through a natural bodily orifice. Laparoscopic surgery is a related type of MIS procedure in which a small incision is formed in the abdomen of a patient and a trocar is inserted through the incision to form a surgical access pathway for a surgical tool and elongate shaft. Once located within the abdomen, the surgical tool engages and/or treats tissue in a number of ways to achieve a diagnostic or therapeutic effect. Manipulation and engagement of the surgical tool may take place via various components passing through the elongate shaft.

One surgical instrument commonly used with a trocar is a surgical clip applier, which can be used to ligate blood vessels, ducts, shunts, or portions of body tissue during surgery. Traditional surgical clip appliers have a handle and an elongate shaft extending from the handle. A pair of movable opposed jaws is positioned at the end of the elongate shaft for holding and forming a surgical or "ligation" clip therebetween. In operation, a user (e.g., a surgeon or clinician) positions the jaws around the vessel or duct and squeezes a trigger on the handle to close the jaws and thereby collapse the surgical clip over the vessel.

More recently, however, robotic systems have been developed to assist in MIS procedures. Instead of directly engaging a surgical instrument, users are now able to operate surgical instruments via an electronic interface in communication with a robotic manipulator. With the advances of robotic surgery, a user need not even be in the operating room with the patient during the surgery.

Robotic surgical systems are also now capable of utilizing robotically controlled clip appliers. Such clip appliers include features for robotically feeding and forming surgical clips. Advances and improvements to the methods and devices for applying surgical clips to vessels, ducts, shunts, etc. is continuously in demand to make the process more efficient and safe.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to surgical systems and, more particularly, to surgical clip appliers with improved jaws and camming mechanisms that facilitate parallel closure of opposed jaw members.

Embodiments discussed herein describe improvements to end effector jaws used in surgical clip appliers. As described herein, an end effector may include a housing with first and second jaw members extending out a distal end of the housing and each comprising an independent structure that is movable relative to the other. A first cam track may be provided on the first jaw member and a second cam track may be provided on the second jaw member. A cam may provide first and second cam surfaces slidably engageable with the first and second cam tracks, respectively, and a biasing device may continuously urge the cam in a distal direction relative to the first and second jaw members. The first and second cam surfaces and the first and second cam tracks may be angled such that axial movement of the cam in the distal direction relative to the first and second jaw members causes the jaw members to close. Proximal tension (biasing force) on the cam (or another cam) urges the jaw members to open.

The embodiments described herein may prove advantageous in providing pre-loaded spring closure, which may ensure consistent clip forming forces may also act as an inherent overload protection to the jaws. Active control of the proximal tension can also provide anti-backup capabilities for the end effector, which may allow a surgeon to stop mid-forming if needed. Moreover, since the jaw members comprise independent structures, substantially parallel closure may be achieved, which effectively eliminates distal tip-to-tip closure of the jaw members. Eliminating tip-to-tip closure eliminates the need to deflect the opposed jaw members between supported ends, which may prove advantageous in eliminating the additional reaction load from the opposing jaw member and minimizing jaw length. Moreover, substantial parallel closure between opposed jaw members may prove advantageous in reducing manufacturing costs. Whereas, conventional clip applier jaws are typically manufactured of robust materials via stamping or machining processes to accommodate the large forces required to fully close the jaws, the jaws described herein require less force to fully close, which allows the jaws to be manufactured of less expensive materials and via less expensive manufacturing processes.

Figure 1:
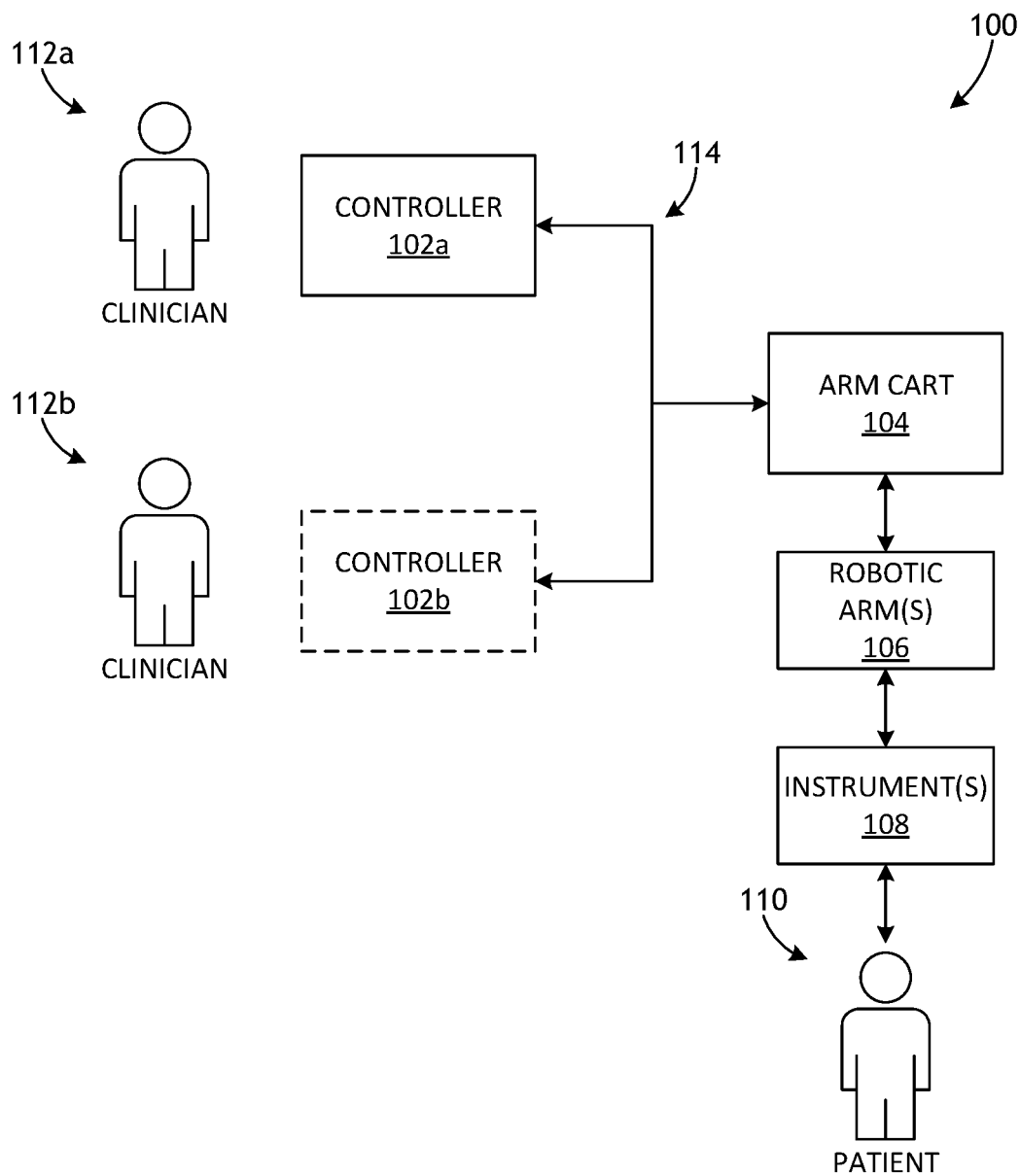
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to a robotic manipulator and, more particularly, to one or more robotic arms 106 or "tool drivers". Each robotic arm 106 may include and otherwise provide a location for mounting one or more surgical tools or instruments 108 for performing various surgical tasks on a patient 110. Operation of the robotic arms 106 and instruments 108 may be directed by a clinician 112a (e.g., a surgeon) from the master controller 102a.

In some embodiments, a second master controller 102b (shown in dashed lines) operated by a second clinician 112b may also direct operation of the robotic arms 106 and instruments 108 in conjunction with the first clinician 112a. In such embodiments, for example, each clinician 102a,b may control different robotic arms 106 or, in some cases, complete control of the robotic arms 106 may be passed between the clinicians 102a,b. In some embodiments, additional arm carts (not shown) having additional robotic arms (not shown) may be utilized during surgery on a patient 110, and these additional robotic arms may be controlled by one or more of the master controllers 102a,b.

The arm cart 104 and the master controllers 102a,b may be in communication with one another via a communications link 114, which may be any type of wired or wireless telecommunications means configured to carry a variety of communication signals (e.g., electrical, optical, infrared, etc.) according to any communications protocol.

The master controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical instrument(s) 108, for example, for opening and closing opposing jaws, applying an electrical potential (current) to an electrode, or the like. The master controllers 102a,b can also include an optional feedback meter viewable by the clinicians 112a,b via a display to provide a visual indication of various surgical instrument metrics, such as the amount of force being applied to the surgical instrument (i.e., a cutting instrument or dynamic clamping member).

Figure 2:
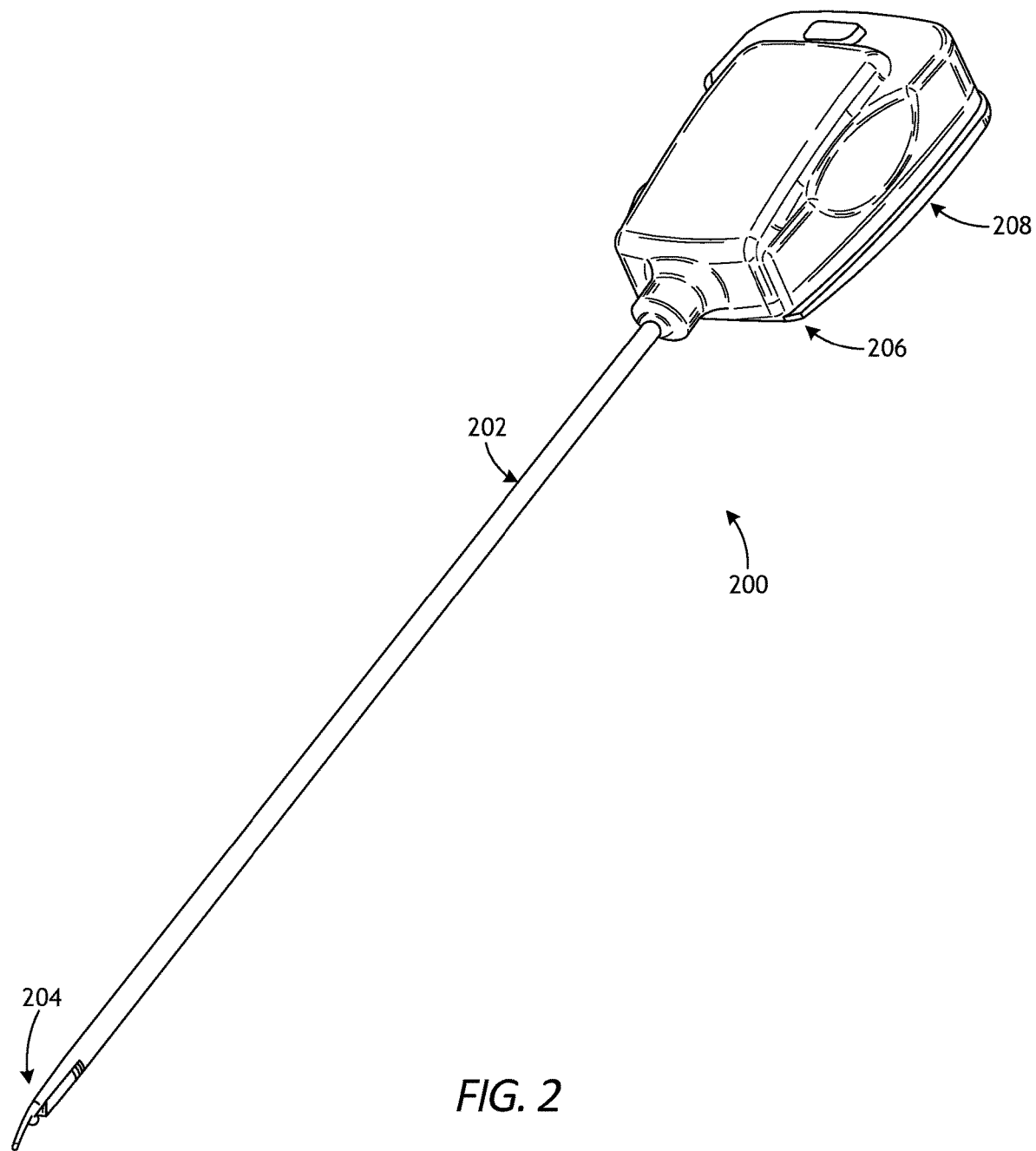
FIG. 2 is an isometric top view of an example surgical tool that may incorporate some or all of the principles of the present disclosure.

FIG. 2 is an isometric top view of an example surgical tool 200 that may incorporate some or all of the principles of the present disclosure. The surgical tool 200 may be the same as or similar to the surgical instrument(s) 108 of FIG. 1 and, therefore, may be used in conjunction with the robotic surgical system 100 of FIG. 1. Accordingly, the surgical tool 200 may be designed to be releasably coupled to a robotic arm 106 (FIG. 1) of a robotic manipulator of the robotic surgical system 100. Full detail and operational description of the surgical tool 200 is provided in co-owned U.S. Pat. No. 10,039,548, entitled "Clip Applier Adapted for Use with a Surgical Robot."

While the surgical tool 200 is described herein with reference to a robotic surgical system, it is noted that the principles of the present disclosure are equally applicable to non-robotic surgical tools or, more specifically, manually operated surgical tools. Accordingly, the discussion provided herein relating to robotic surgical systems merely encompasses one example application of the presently disclosed inventive concepts.

As illustrated, the surgical tool 200 can include an elongate shaft 202, an end effector 204 coupled to the distal end of the shaft 202, and a drive housing 206 coupled to the proximal end of the shaft 202. The terms "proximal" and "distal" are defined herein relative to a robotic surgical system having an interface configured to mechanically and electrically couple the surgical tool 200 (e.g., the drive housing 206) to a robotic manipulator. The term "proximal" refers to the position of an element closer to the robotic manipulator and the term "distal" refers to the position of an element closer to the end effector 204 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

In applications where the surgical tool 200 is used in conjunction with a robotic surgical system (e.g., system 100 of FIG. 1), the drive housing 206 can include a tool mounting portion 208 designed with features that releasably couple the surgical tool 200 to a robotic arm (e.g., the robotic arms 106 or "tool drivers" of FIG. 1) of a robotic manipulator. The tool mounting portion 208 may releasably attach (couple) the drive housing 206 to a tool driver in a variety of ways, such as by clamping thereto, clipping thereto, or slidably mating therewith. In some embodiments, the tool mounting portion 208 may include an array of electrical connecting pins, which may be coupled to an electrical connection on the mounting surface of the tool driver. While the tool mounting portion 208 is described herein with reference to mechanical, electrical, and magnetic coupling elements, it should be understood that a wide variety of telemetry modalities might be used, including infrared, inductive coupling, or the like.

Figure 3:
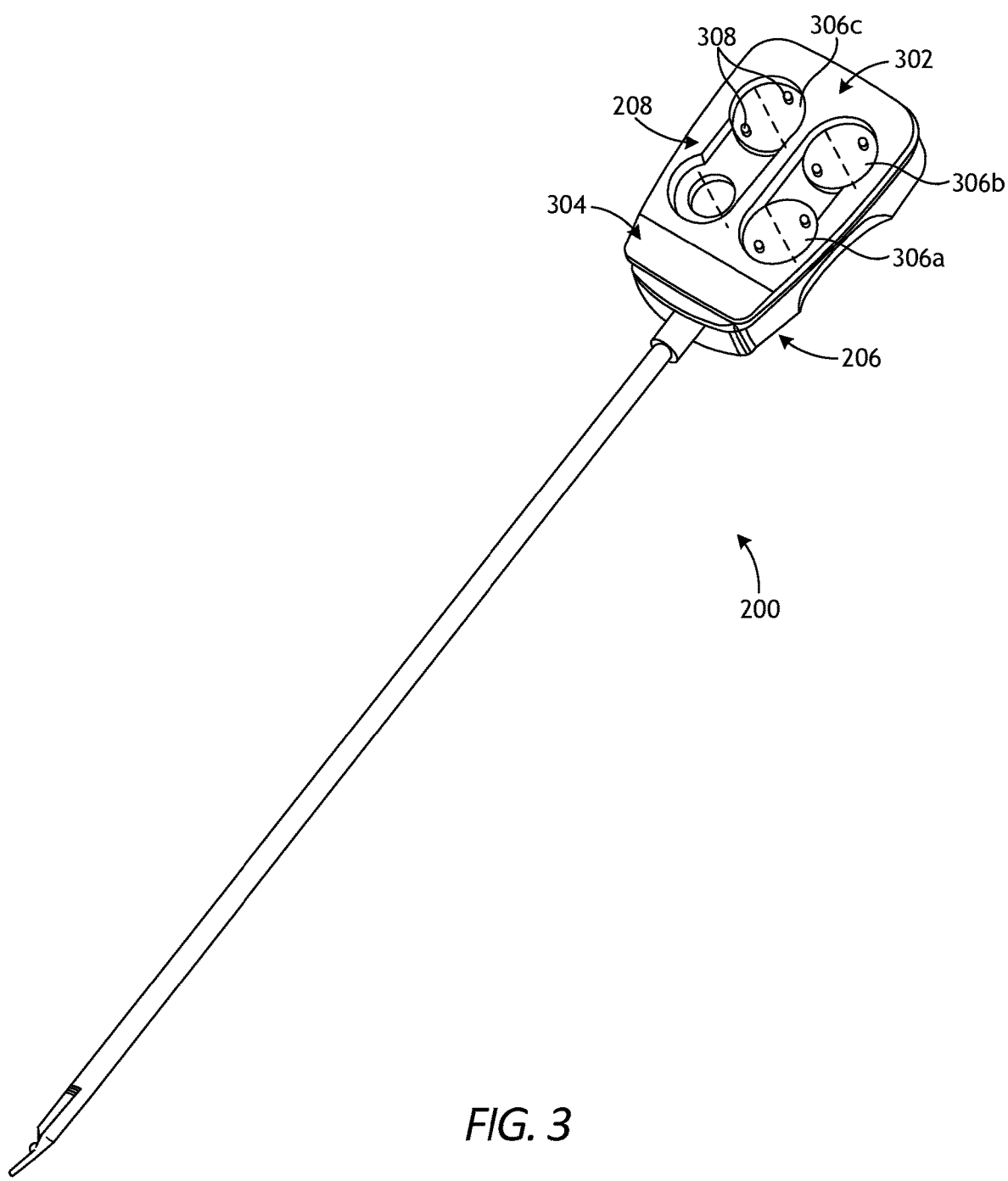
FIG. 3 is an isometric bottom view of the surgical tool of FIG. 2.

FIG. 3 is an isometric bottom view of the surgical tool 200. The surgical tool 200 further includes an interface 302 that mechanically and electrically couples the tool mounting portion 208 to a robotic manipulator. In various embodiments, the tool mounting portion 208 includes a tool mounting plate 304 that operably supports a plurality of drive inputs, shown as a first drive input 306a, a second drive input 306b, and a third drive input 306c. While only three drive inputs 306a-c are shown in FIG. 3, more or less than three may be employed, without departing from the scope of the disclosure.

In the illustrated embodiment, each drive input 306a-c comprises a rotatable disc configured to align with and couple to a corresponding input actuator (not shown) of a given tool driver. Moreover, each drive input 306a-c provides or defines one or more surface features 308 configured to align with mating surface features provided on the corresponding input actuator. The surface features 308 can include, for example, various protrusions and/or indentations that facilitate a mating engagement.

Figure 4:
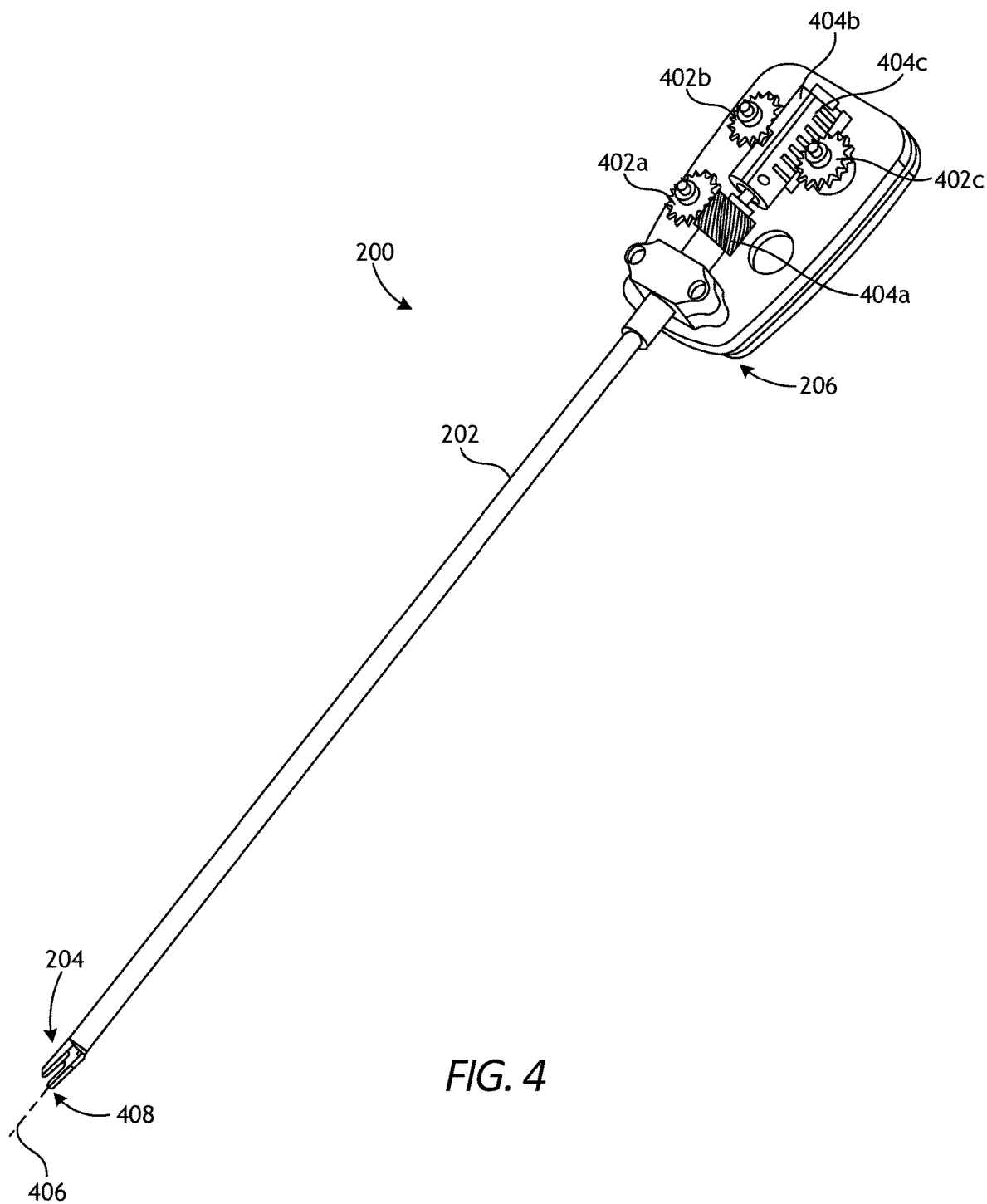
FIG. 4 is an exposed isometric view of the surgical tool of FIG. 2.

FIG. 4 is an exposed isometric view of the surgical tool 200. The shroud that covers the drive housing 206 has been removed to reveal the internal component parts. As illustrated, the surgical tool 200 may include a first drive gear 402a, a second drive gear 402b, and a third drive gear 402c. The first drive gear 402a may be operatively coupled to (or extend from) the first drive input 306a (FIG. 3) such that actuation of the first drive input 306a correspondingly rotates the first drive gear 402a. Similarly, the second and third drive gears 402b,c may be operatively coupled to (or extend from) the second and third drive inputs 306b,c (FIG. 3), respectively, such that actuation of the second and third drive inputs 306b,c correspondingly rotates the second and third drive gears 402b,c, respectively.

The first drive gear 402a may be configured to intermesh with a first driven gear 404a, which is operatively coupled to the shaft 202. In the illustrated embodiment, the driven gear 404a comprises a helical gear. In operation, rotation of the first drive gear 402a correspondingly rotates the first driven gear 404a about a longitudinal axis 406 of the shaft 202. The first driven gear 404a is coupled to the shaft 202 such that rotation of the first drive gear 402a controls rotation of the shaft 202 in clockwise and counter-clockwise directions based on the rotational direction of the first drive gear 402a.

The second drive gear 402b may be configured to intermesh with a second driven gear 404b (partially visible in FIG. 4), and the third drive gear 402c may be configured to intermesh with a third driven gear 404c. In the illustrated embodiment, the second and third drive and driven gears 402b,c and 404b,c comprise corresponding rack and pinion interfaces, where the driven gears 404b,c comprise the rack and the drive gears 402b,c comprise the pinion. Independent rotation of the second and third drive gears 402b,c will cause the second and third driven gears 404b,c, respectively, to translate linearly relative to (independent of) one another.

In the illustrated embodiment, the end effector 204 comprises a surgical clip applier having opposing jaws 408. In at least one embodiment, actuation (rotation) of the third drive gear 402c will result in a surgical clip (not shown) being fed into the jaws 408. Rotation of the third drive gear 402c may be precisely controlled by an electrical and software interface to deliver the exact linear travel to the third driven gear 404c necessary to feed a clip 416 into the jaws 408. Upon delivery of a clip into the jaws 408, or after a predetermined amount of rotation of the third drive gear 402c, rotation of the third drive gear 402c is reversed in a second angular direction to move the third driven gear 404c linearly in a proximal direction, which allows the clip feeding process to be repeated.

Actuation of the second drive gear 402b causes the jaws 408 to close or collapse to crimp a surgical clip residing therebetween. Once the surgical clip is successfully deployed (crimped), rotation of the second drive gear 402b is reversed in the opposite angular direction to move the second driven gear 404b in a proximal direction, which permits the jaws 408 to open once again in preparation for receiving another surgical clip. The process may be repeated several times to feed and crimp a predetermined number of clips residing in the shaft 202.

It should be noted that the processes of delivering a surgical clip into the jaws 408 and collapsing the jaws 408 to crimp the surgical clip are not limited to the actuation mechanisms and structures described herein. In alternative embodiments, for example, the second and third driven gears 404b,c may instead comprise capstan pulleys configured to route and translate drive cables within the shaft 202. In such embodiments, the drive cables may be operatively coupled to one or more lead screws or other types of rotating members positioned within the shaft 202 near the distal end and capable of advancing a feedbar that delivers a surgical clip into the jaws 408 and advancing a cam to collapse the jaws 408 and crimp the surgical clip.

Figure 5:
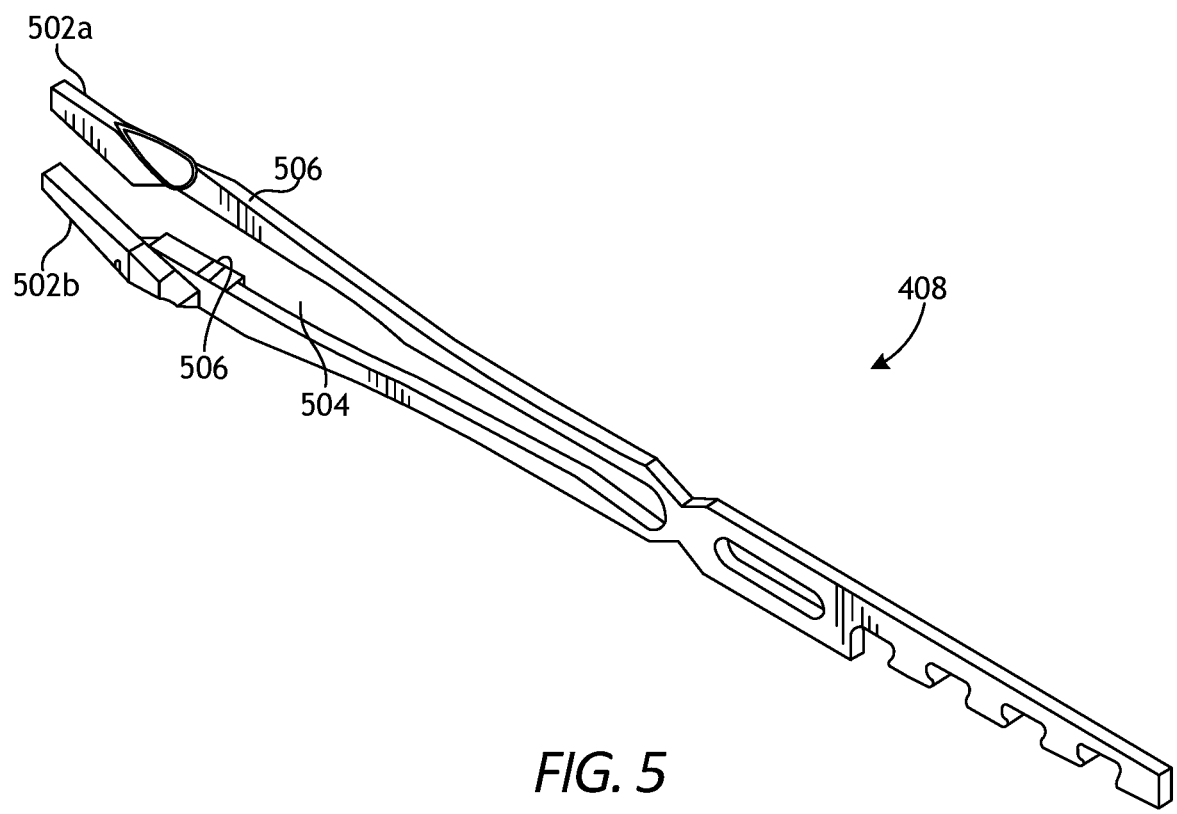
FIG. 5 is an enlarged, isometric view of one example of the jaws of FIG. 4.

FIG. 5 is an enlarged, isometric view of one example of the jaws 408 of FIG. 4. As illustrated, the jaws 408 comprise a one-piece architecture having opposed first and second jaw members 502a and 502b with a gap 504 defined therebetween. The first and second jaw members 502a,b are movable relative to one another and adapted to receive a surgical clip (not shown) therebetween. In at least one embodiment, the jaw members 502a,b are biased to an open position, and a force is required to move the jaw members 502a,b toward one another (i.e., collapse the jaws 408). In some applications, each jaw member 502a,b can include a groove formed on opposed inner surfaces thereof for receiving the legs of a surgical clip in alignment with the jaw members 502a,b. Each jaw member 502a,b can also include a cam track 506 formed thereon. In the illustrated embodiment, the cam tracks 506 are essentially ramped features formed on a superior (upper) surface of each jaw member 502a,b. A cam 600 (FIG. 6) may be configured to engage the cam tracks 506 and thereby urge (force) the jaw members 502a,b to collapse toward one another.

Figure 6:
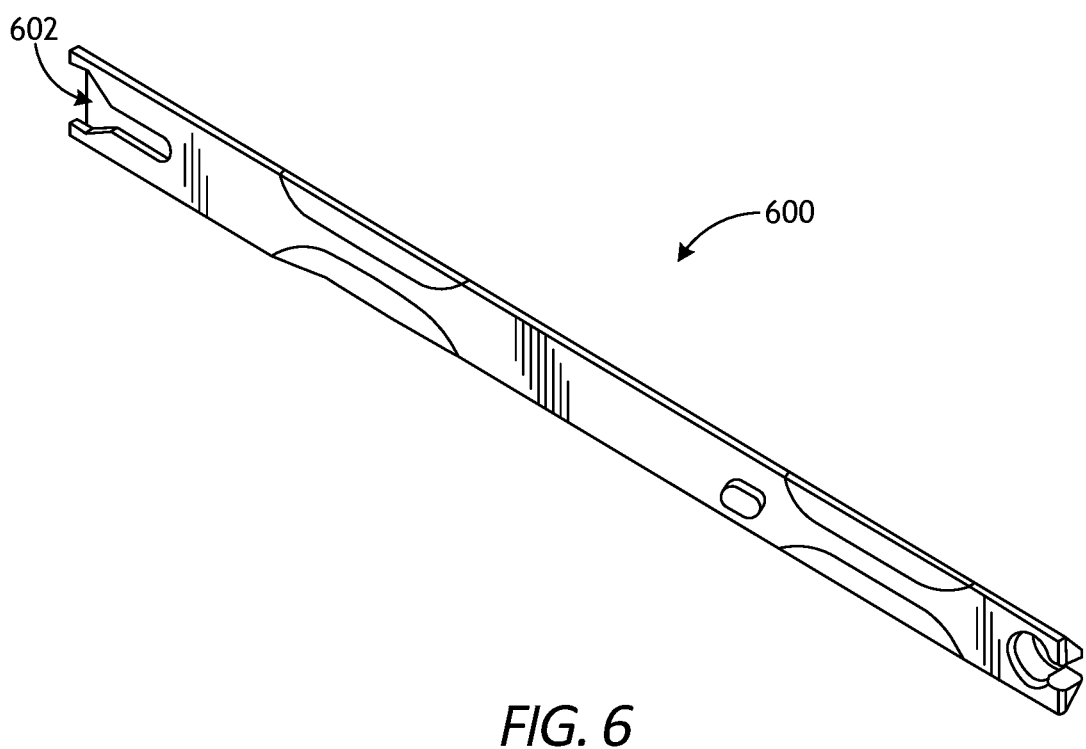
FIG. 6 is an enlarged isometric view of an example cam.

FIG. 6 is an enlarged isometric view of one example of the cam 600. The cam 600 may be configured for slidably mating with and engaging the jaw members 502a,b (FIG. 6). More specifically, the cam 600 may provide or otherwise define a camming channel 602 adapted to engage and actuate the jaws 408 (FIGS. 4-5). As illustrated, the camming channel 602 forms a tapering recess. During actuation, the camming channel 602 is configured to slidably receive the cam tracks 506 (FIG. 5) provided by the jaw members 502a,b (FIG. 5). Distal movement of the cam 600 relative to the jaws 408 will urge the jaw members 502a,b to collapse toward each other.

Figure 7A:
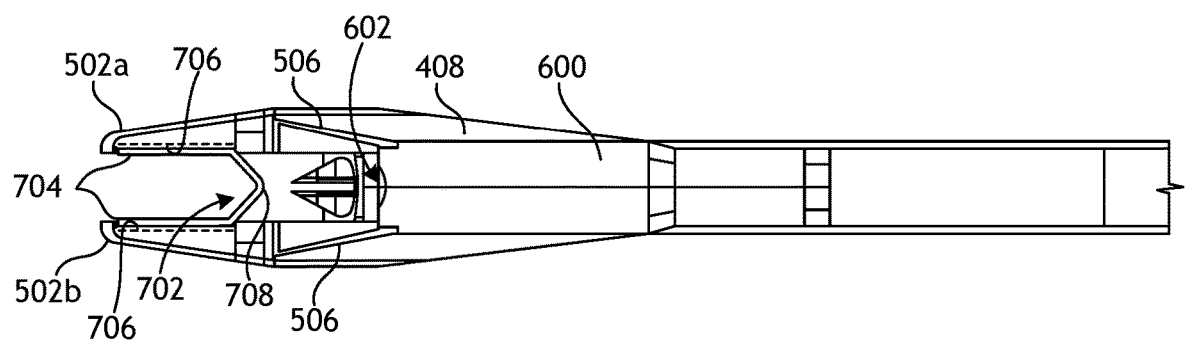
FIGS. 7A and 7B illustrate example operation of the cam and the jaws.
Figure 7B:
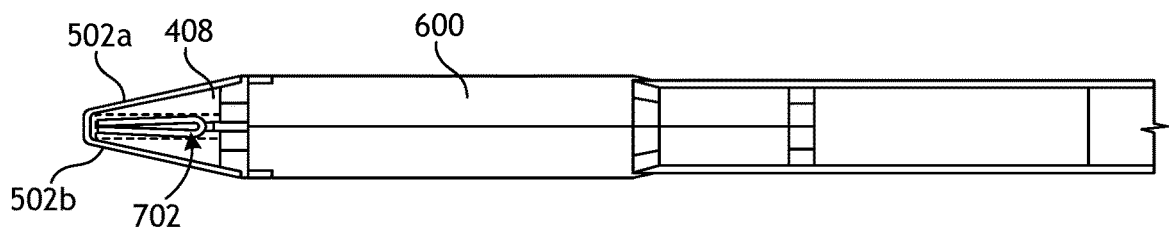

FIGS. 7A and 7B illustrate example operation of the cam 600 and the jaws 408. In FIG. 7A, a surgical clip 702 has been previously advanced into the jaws 408. As illustrated, the legs 704 of the surgical clip 702 are received within grooves 706 defined in the opposed inner surfaces of the jaw members 502a,b, and the crown 708 (alternately referred to as the "apex") is positioned between the jaw members 502a,b and points proximally.

To crimp the surgical clip 702, the cam 600 is advanced distally (i.e., to the left in FIGS. 7A-7B) relative to the jaws 408. In FIG. 7A, the cam 600 is shown in a proximal position, where the jaw members 502a,b are spaced apart from one another. As the cam 600 is advanced distally over the jaw members 502a,b, the camming channel 602 receives and slidingly engages the angled surfaces of the cam tracks 506, which simultaneously urges the jaw members 502a,b to collapse toward one another and crimp the surgical clip 702. FIG. 7B shows the crimped surgical clip 702.

During distal movement of the cam 600, the jaw members 502a,b act as individual cantilever beams as they are urged toward one another by the cam 600. Because the jaw members 502a,b act as cantilever beams, the distal ends or "tips" of the jaw members 502a,b come together first, at which point each jaw member 502a,b is effectively converted into a fixed-pinned beam, which increases the stiffness of the system. As opposed fixed-pinned beams, the lateral force required to fully close the jaw members 502a,b along the length of the grooves 608 increases dramatically. In some applications, for example, 60 lbf-100 lbf of force is required to fully close the jaw members 502a,b. Consequently, this requires more expensive and powerful actuators to move (actuate) the cam 600 and necessitates more robust materials used to make the jaws 408, the cam 600, and other intervening structural elements that facilitate jaw actuation.

According to embodiments of the present disclosure, robotic clip appliers (or alternately non-robotic clip appliers) may incorporate improved jaws that eliminate distal tip-to-tip closure of its corresponding jaw members. As described herein, the improved jaws may be designed to achieve parallel (or substantially parallel) closure between the corresponding jaw members. As used herein, the term "substantially parallel" can refer to true relative parallelism between opposing members or near true relative parallelism, without departing from the scope of the disclosure. Eliminating tip-to-tip closure eliminates the need to deflect the opposed jaw members between supported ends, which may eliminate the additional reaction load from the opposing jaw member and minimize jaw length. Moreover, substantial parallel closure between opposed jaw members may reduce manufacturing costs. Conventional clip applier jaws, such as the jaws 408 of FIG. 5 for example, are typically manufactured of robust materials via stamping or machining processes to accommodate the large forces required to fully close the jaws. In contrast, jaws capable of facilitating parallel closure may require less force to fully close, which allows the jaws to be manufactured of less expensive materials and via less expensive manufacturing processes.

Figure 8A:
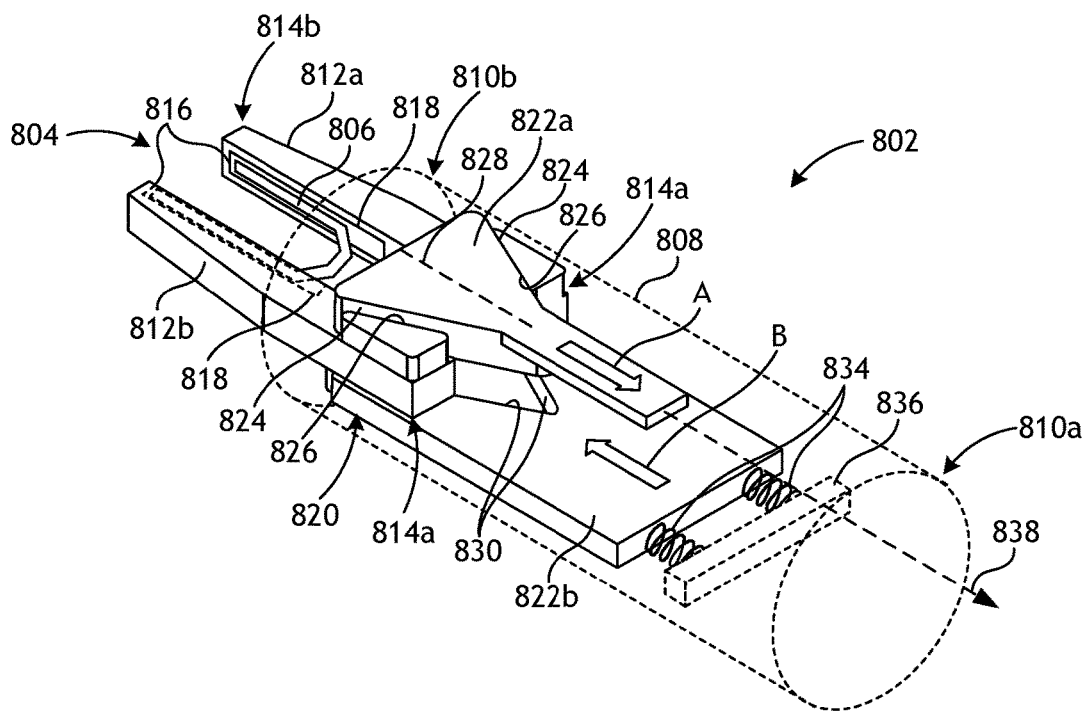
FIGS. 8A and 8B are isometric top and bottom view of an example end effector that may incorporate the principles of the present disclosure.
Figure 8B:
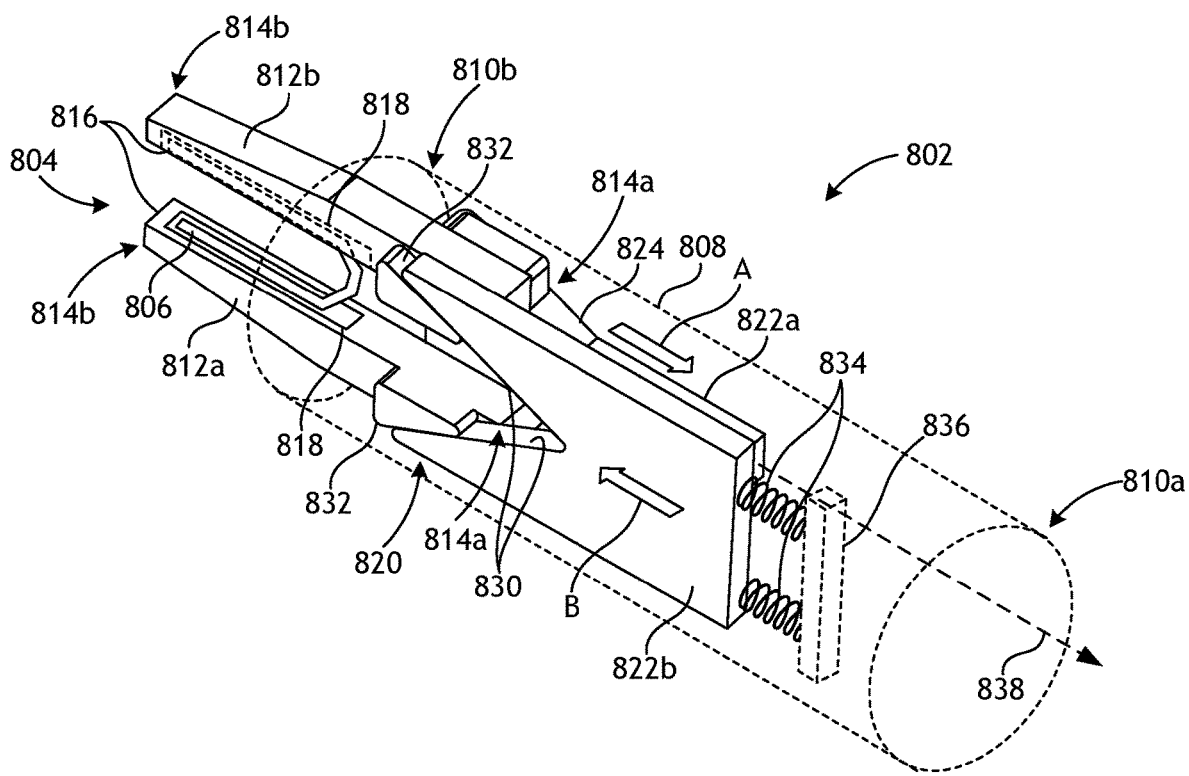

FIGS. 8A and 8B are isometric top and bottom views, respectively, of an example end effector 802 that may incorporate the principles of the present disclosure, according to one or more embodiments. The end effector 802 may be similar in some respects to the end effector 204 of FIG. 2 and, therefore, may be incorporated into the surgical tool 200 described herein. Moreover, the end effector 802 may comprise a clip applier having opposing jaws 804 that are actuatable to collapse toward one another to crimp a surgical clip 806. The jaws 804 may be similar in some respects to the jaws 408 of FIGS. 4-5 and may replace the jaws 408 in any of the above-described embodiments.

As illustrated, the end effector 802 may include a housing 808 (shown in dashed lines) having a proximal end 810a and a distal end 810b. The housing 808 may at least partially surround most of the component parts of the end effector 802. In some embodiments, the housing 808 may form part of and otherwise comprise an axial extension of the shaft 202 of the surgical tool 200 of FIG. 2. In other embodiments, however, the housing 808 may comprise an independent structure and the proximal end 810a may be coupled to the distal end of the shaft 202. In yet other embodiments, the proximal end 810a may be operatively coupled to an articulable wrist joint that enables the end effector 802 and the jaws 804 to articulate during operation. In such embodiments, the end effector 802 may be positioned distal to the articulable wrist joint.

As illustrated, the jaws 804 comprise a two-piece assembly that includes opposing jaw members 812a and 812b. The jaw members 812a,b extend out of or otherwise protrude from the distal end 810b of the housing 808. Each jaw member 812a,b is an independent structure that is movable relative to the other upon actuation to transition the jaws 804 between open and closed positions. As illustrated, each jaw member 812a,b comprises an elongate body having a first or proximal end 814a and a second or distal end 814b.

Surgical clips 806 (one shown) may be received between the jaw members 812a,b at or near the distal end 814b for crimping. More specifically, surgical clips 806 may be fed into and otherwise received between opposed inner surfaces 816 of the jaw members 812a,b provided near the distal end 814b. In some embodiments, a groove 818 may be defined on the inner surface 816 of each jaw member 812a,b and configured to receive the opposing legs of the surgical clip 806 in alignment with the jaw members 812a,b. In other embodiments, however, the grooves 818 may be omitted and the surgical clip 806 may alternatively be maintained between the opposing inner surfaces 816 via an interference fit or the like.

In contrast to the design and function of conventional clip applier jaws (e.g., the jaws 408 of FIGS. 4-5), which commonly employ one-piece opposing jaw members with a gap defined therebetween, the discrete and individual jaw members 812a,b described herein allow the jaws 804 to achieve parallel closure, which may prove advantageous in reducing the amount of force required to collapse the jaw members 812a,b to the closed position. As used herein, the phrase "parallel closure" refers to the relative parallel disposition of the opposing inner surfaces 816 of the jaw members 812a,b throughout the entire range of motion as the jaw members 812a,b move between open and closed positions. "Parallel closure" is often used with respect to medical device end effectors and is desirable to achieve to minimize tissue damage due to non-uniform pressure or milking (squeezing out) of tissue from between opposed jaw members. Because the jaw members 812a,b are separate and independent structures that are movable relative to one another during actuation, the inner surfaces 816 are able to maintain a parallel or substantially parallel correlation (juxtaposition) while collapsing toward the closed position and crimping the surgical clip 806.

To help achieve parallel closure, the end effector 802 includes an actuation mechanism 820 operatively coupled to the jaw members 812a,b and actuatable to transition the jaw members 812a,b between the open and closed positions. As used herein, the phrase "operatively coupled" can refer to a direct or indirect coupling or sliding relationship between two structural members.

In the illustrated embodiment, the actuation mechanism 820 includes a first or "upper" cam 822a and a second or "lower" cam 822b. The upper and lower cams 822a,b, may be at least partially housed within the housing 808. In some embodiments, as illustrated, the upper cam 822a may be offset a short distance from the lower cam 822b. In other embodiments, however, the upper cam 822a may rest on the upper surface of the lower cam 822b, without departing from the scope of the disclosure. Relative movement of the upper and lower cams 822a,b may cause the jaws 804 to open and close during actuation.

As best seen in FIG. 8A, the upper cam 822a includes opposing outer cam surfaces 824 matable and slidably engageable with upper cam tracks 826 defined by or otherwise provided on the upper surface each jaw member 812a,b at or near the proximal end 814a. The outer cam surfaces 824 and the upper cam tracks 826 may each define opposing surfaces that are angled relative to a centerline 828 (FIG. 8A) such that axial movement of the upper cam 822a in a proximal direction A relative to the jaw members 812a,b causes the jaw members 812a,b to open or otherwise separate laterally from each other. As will be appreciated, the magnitude of the angled surfaces relative to the centerline 828 will directly impact the opening movement of the jaw members 812a,b. More specifically, a smaller angle relative to the centerline 828 will cause the jaw members 812a,b to open more slowly as the upper cam 822a moves proximally relative to the jaw members 812a,b. In contrast, a larger angle relative to the centerline 828 will cause the jaw members 812a,b to open more quickly as the upper cam 822a moves proximally relative to the jaw members 812a,b. The angles of the surfaces of the outer cam surfaces 824 and the upper cam tracks 826 relative to the centerline 828 may range between about 10° and about 45°.

Similarly, the lower cam 822b includes opposing inner cam surfaces 830 matable and slidably engageable with lower cam tracks 832 (FIG. 8B) defined by or otherwise provided on the bottom surface each jaw member 812a,b at or near the proximal end 814a. The inner cam surfaces 830 and the lower cam tracks 832 may each define opposing surfaces that are angled relative to the centerline 828 (FIG. 8A) such that axial movement of the lower cam 822b in a distal direction B relative to the jaw members 812a,b causes the jaw members 812a,b to close. The magnitude of the angled surfaces relative to the centerline 828 will directly impact the closing movement of the jaw members 812a,b. More specifically, a smaller (steeper) angle relative to the centerline 828 will cause the jaw members 812a,b to close more quickly as the lower cam 822b moves distally relative to the jaw members 812a,b. In contrast, a larger (lower) angle relative to the centerline 828 will cause the jaw members 812a,b to close more slowly as the lower cam 822b moves distally relative to the jaw members 812a,b. The angles of the surfaces of the inner cam surfaces 830 and the lower cam tracks 832 relative to the centerline 828 may range between about 10° and about 45°.

The opposing angled surfaces of the outer cam surfaces 824 and the upper cam tracks 826 and of the inner cam surfaces 830 and the lower cam tracks 832 may provide a lubricious interface to mitigate or eliminate friction between the upper and lower cams 822a,b and the jaw members 812a,b. In some embodiments, a liquid-based or powder-based lubricant may be applied to some or all of the angled surfaces. Suitable lubricants include, but are not limited to, polytetrafluoroethylene (PTFE) derived lubricants (e.g., DryFilm RA, DURAGLIDE™, etc.), sodium stearate, silicone, tungsten disulfide, graphite, or any combination thereof. In other embodiments, some or all of the angled surfaces may be polished to reduce or eliminate friction.

The actuation mechanism 820 may further include one or more biasing devices 834 (two shown) configured to continuously bias the jaws 804 toward the closed position. In the illustrated configuration, the biasing devices 834 are depicted as compression or coil springs, but may alternatively comprise a series of Belleville washers, a magnet arrangement, an elastomer, a combination thereof, or any other type of biasing mechanism capable of applying a passive spring load. While two biasing devices 834 are depicted, more or less than two may be employed, without departing from the scope of the disclosure.

In the illustrated embodiment, the biasing devices 834 act on the lower cam 822b and provide a passive spring load that continuously urges the lower cam 822b distally relative to the jaw members 812a,b, which causes the inner cam surfaces 830 to slidably engage the lower cam tracks 832 of the jaw members 812a,b and thereby urge the jaws 804 toward the closed position. In some embodiments, as illustrated, the biasing devices 834 may interpose the lower cam 822b and a stop member 836 arranged proximal to the lower cam 822b. The stop member 836 may comprise any stationary (static) structural element that the biasing devices 834 may engage to provide the passive spring load on the lower cam 822b.

In some embodiments, as illustrated, the stop member 836 may be included in the end effector and otherwise located (secured) within the housing 808. In other embodiments, however, the stop member 836 may alternatively be located proximal to the end effector 802. In such embodiments, for example, the stop member 836 may be located within or otherwise comprise any static structure within a drive housing (e.g., the drive housing 206 of FIG. 2). In such embodiments, the lower cam 822b may be operatively coupled to a rigid or semi rigid drive shaft (or rod) that extends from the drive housing, or alternatively a portion of the lower cam 822b may instead extend to the drive housing. The biasing devices 834 may be arranged to engage the drive shaft (or the proximal end of the lower cam 822b) to urge the lower cam 822b in the distal direction B.

To prevent the jaws 804 from closing or remaining at the closed position, the upper cam 822a may be selectively urged in the proximal direction A, which causes the outer cam surfaces 824 to slidably engage the upper cam tracks 826 of the jaw members 812a,b and thereby urge the jaws 804 toward the open position. In some embodiments, one or more flexible members 838 (one shown as a dashed line) may be operatively coupled to the upper cam 822a and extend proximally to a drive housing (e.g., the drive housing 206 of FIG. 2). At the drive housing, the flexible member 838 may be operatively coupled to a drive input actuatable to urge (pull) the upper cam 822a in the proximal direction A and thereby maintain the upper cam 822a in proximal tension. The flexible member 838 may comprise, for example, a drive cable or a flexible shaft. The flexible member 838 may prove advantageous in embodiments where the end effector 802 is arranged distal to an articulable wrist joint, and the flexible member 838 may be able to extend through the articulable wrist joint.

In other embodiments, however, the upper cam 822a may be operatively coupled to a rigid or semi rigid drive shaft (or rod) that extends from a drive housing (e.g., the drive housing 206 of FIG. 2). Alternatively, a portion of the upper cam 822a itself may instead extend to the drive housing. In such embodiments, the drive shaft (or the proximal end of the upper cam 822a) may be operatively coupled to a drive input at the drive housing that urges the upper cam 822a in the proximal direction A and thereby maintains the upper cam 822a in proximal tension.

Accordingly, because of the passive spring load of the biasing device(s) 834, the natural or "dead state" of the end effector 802 may be with the jaws 804 in the closed position. Those skilled in the art will readily appreciate that this is counterintuitive to robotics engineering, which ordinarily dictates that the dead state for any surgical tool should be in an open position. The upper cam 822a, however, may be maintained in proximal tension and the end effector 802 may also have one or more failsafes or bailout mechanisms that will allow the jaws 804 to open manually, if needed. Moreover, whereas conventional clip appliers require "push" closure (normally embodied by means of a lead screw, which eats up precious space distal of an articulation joint), the end effector 802 utilizes proximal tension (biasing force) on the upper cam 822a, which when released, allows for the passive spring load applied by the lower cam 822b to crimp surgical clips.

Figure 8C:
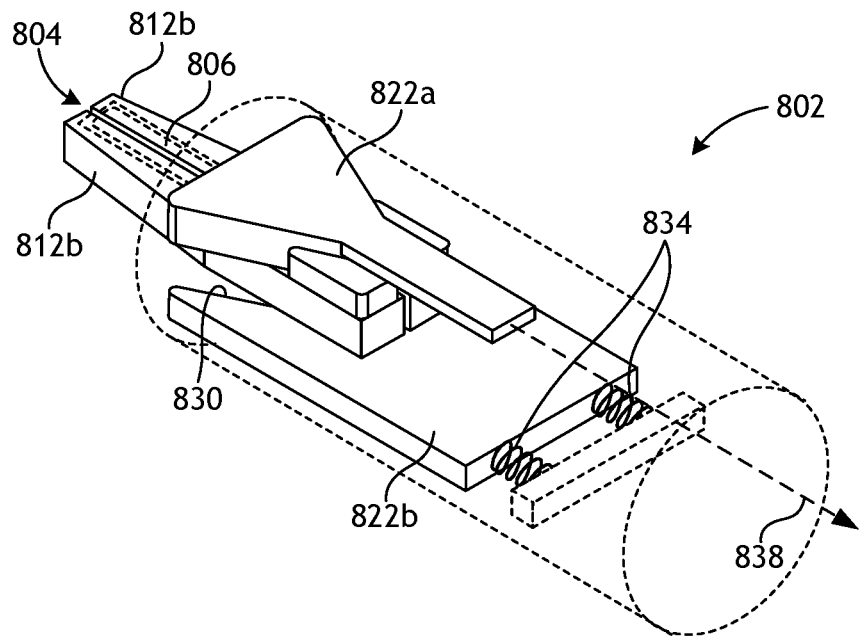
FIG. 8C is another isometric top view of the end effector of FIGS. 8A-8B.

FIG. 8C is another isometric top view of the end effector 802. Referring to FIGS. 8A-8C, example operation of the end effector 802 is now provided. FIGS. 8A-8B show the jaws 804 in the open position, and FIG. 8C depicts the jaws 804 after having been moved (actuated) to a closed position.

In FIGS. 8A-8B, the surgical clip 806 may be received between the jaw members 812a,b when the jaws 804 are in the open position. Opening the jaws 804 may be accomplished by placing a tensile load on the upper cam 822a in the proximal direction A, and thereby causing the outer cam surfaces 824 to slidably engage the upper cam tracks 826 of the jaw members 812a,b. Opening the jaws 804 simultaneously causes the inner cam surfaces 830 of the lower cam 822b to slidably engage the lower cam tracks 832 of the jaw members 812a,b, which correspondingly urges the lower cam 822b in the proximal direction A. Moving the lower cam 822b in the proximal direction A builds up spring force in the biasing devices 834 as engaged against the lower cam 822b. The jaws 804 will be held in the open position as long as proximal tension (biasing force) is maintained on the upper cam 822a.

FIG. 8C shows the surgical clip 806 (shown in dashed lines) crimped between the opposing jaw members 812a,b as the jaws 804 collapse toward each other during actuation. To move the jaws 804 to the closed position, and thereby crimp (crush) the surgical clip 806, proximal tension (bias) on the upper cam 822a may be released, which allows upper cam 822a to move distally relative to the jaw members 812a,b. The spring force of the biasing devices 834 may then be able to urge the lower cam 822b in the distal direction B, and moving the lower cam 822b distally causes the inner cam surfaces 830 of the lower cam 822b to slidably engage the lower cam tracks 832 (FIG. 8B) of the jaw members 812a,b, and thereby urge the jaws 804 toward the closed position to crimp the surgical clip 806. Once the surgical clip 806 is crimped, proximal tension (bias) on the upper cam 822a may be initiated once more to move the jaw members 812a,b proximally to the open position in preparation for receiving another surgical clip.

In an alternative embodiment of the end effector 802, proximal tension (bias) may be maintained on both the upper and lower cams 822a,b to open the jaws 804, and the one or more biasing devices 834 may act on both the upper and lower cams 822a,b to provide a passive spring load that continuously urges the upper and lower cams 822a,b distally relative to the jaw members 812a,b. In such embodiments, maintaining the proximal tension (bias) on the upper and lower cams 822a,b keeps the jaws 804 open, and releasing the proximal tension (biasing force) allows the biasing devices 834 to move the upper and lower cams 822a,b distally and thereby close the jaws 804 and crimp the surgical clip.

Relative movement of the opposing jaw members 812a,b allows the planar inner surfaces 816 of each jaw member 812a,b to approach each other in a parallel or substantially parallel trajectory, and thereby provides a simultaneous and uniform crimping of the surgical clip 806. Compared to conventional clip applier jaws, the presently described jaws 804 may prove advantageous for a variety of reasons. Conventional jaws have jaw members that act as cantilever beams as they are forced together during actuation. This results in the distal ends or tips of the jaw members touching first during actuation. Once the tips touch, the jaw members are effectively converted into continuous metal beams supported at each end instead of having a free end. As a result, a great deal of additional force is required to deform the middle of the jaw members to achieve full collapse of the jaws. Testing has shown that upwards of 60-100 lbf of force is required to fully collapse the jaw members of conventional jaws to crimp a surgical clip. The required elevated force necessitates more powerful actuators and more robust materials and manufacturing methods so that the jaws may withstand such forces.

In contrast, the presently described jaw members 812a,b comprise separate structures that allow the jaws 804 to achieve parallel closure and uniform crimping of the surgical clip 806. Parallel closure dramatically reduces the force required to collapse the jaw members 812a,b. In some applications, for example, the required force to adequately collapse (crimp) the surgical clip 806 would be an order of magnitude or less than conventional jaws. This advantageously allows smaller actuators to be used to collapse the jaws 804. Moreover, this allows the jaws 804 to be made of less-expensive materials and manufactured through less-expensive manufacturing processes. In some embodiments, for example, the jaws 804 may be made of injection molded plastic. In other embodiments, the jaws 804 may be made of a metal and molded through a metal injection molding process. In yet other embodiments, the jaws 804 may be made of a plastic or a metal and manufactured via an additive manufacturing process (e.g., 3D printing). In even further embodiments, the jaws 804 may be made of a metallic base with a plastic overmolding, without departing from the scope of the disclosure.

The novel features of the jaws 804 may also prove advantageous in helping to minimize the length and overall size of the jaws 804. More specifically, since less force is required to collapse the jaws 804, less jaw length is required to help deflect a cantilever beam-type jaw member. Consequently, the length of the jaws 804 can be reduced, which may minimize the length of a clip applier past an articulation joint or wrist, for example. Another advantage of the separate jaw members 812a,b is that surgical clips need not be introduced into the jaw members 812a,b out of plane, i.e., from a different elevation within the end effector 802. Rather, the surgical clips can be advanced distally in the same plane as the jaw members 812a,b and pass between the space that separates the jaw members 812a,b.

Figure 9A:
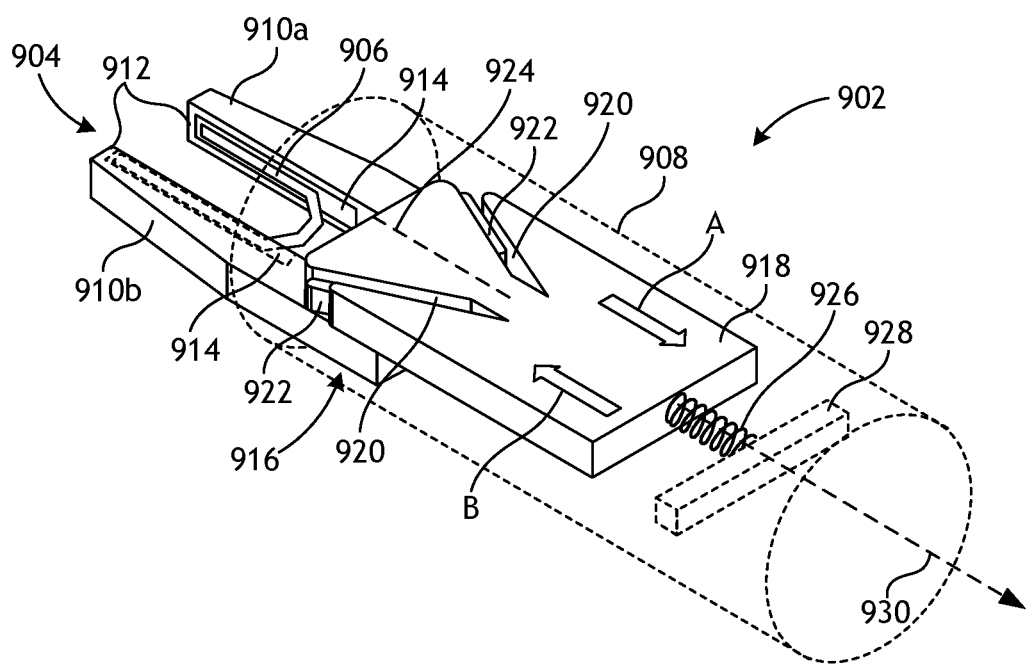
FIGS. 9A and 9B are partial cross-sectional views of another example end effector that may incorporate the principles of the present disclosure, according to one or more embodiments.
Figure 9B:
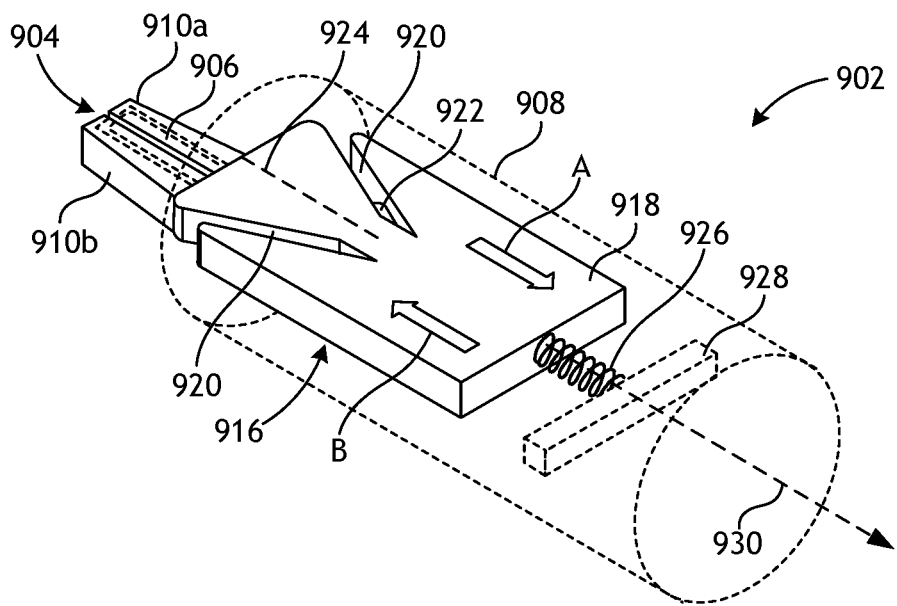

FIGS. 9A and 9B are partial cross-sectional views of another example end effector 902 that may incorporate the principles of the present disclosure, according to one or more embodiments. The end effector 902 may be similar in some respects to the end effector 802 of FIGS. 8A-8C and may therefore be best understood with reference thereto. Moreover, the end effector 902 may replace the end effector 204 of FIG. 2 and may thus be incorporated into the surgical tool 200 of FIG. 2.

As illustrated, the end effector 902 may comprise a clip applier having jaws 904 that are actuatable to collapse toward one another to crimp a surgical clip 906. The end effector 902 may further include a housing 908 that may at least partially surround most of the component parts of the end effector 902. The housing 908 may be similar to or the same as the housing 808 of FIGS. 8A-8C, and therefore will not be described again in detail.

The jaws 904 may be similar in some respects to the jaws 804 of FIGS. 8A-8C. For instance, similar to the jaws 804, the jaws 904 may also comprise a two-piece assembly that includes opposing jaw members 910a and 910b that are independent structures movable relative to the other upon actuation. Surgical clips 906 may be fed into and otherwise received between opposed inner surfaces 912 (FIG. 9A) of the jaw members 910a,b and, in some embodiments, a groove 914 (FIG. 9A) may be defined on the inner surface 912 of each jaw member 910a,b to receive the opposing legs of the surgical clip 906. The discrete and individual jaw members 910a,b described herein allow the jaws 904 to achieve parallel closure between the opposing inner surfaces 912.

To help achieve parallel closure, the end effector 902 may further include an actuation mechanism 916 operatively coupled to the jaw members 910a,b and actuatable to transition the jaw members 910a,b between the open and closed positions. In the illustrated embodiment, the actuation mechanism 916 includes a cam 918 at least partially housed within the housing 908. Movement of the cam 918 relative to the jaw members 910a,b may cause the jaws 904 to open and close during actuation.

As illustrated, the cam 918 includes opposing cam surfaces 920 matable and slidably engageable with cam tracks 922 defined by or otherwise provided on each jaw member 910a,b. In the illustrated embodiment, the cam surfaces 920 comprise angled slots defined in the cam 918 and are sized to receive the corresponding cam tracks 922. The cam tracks 922 are depicted as protrusions or projections defined on the upper surface of the jaw members 910a,b, but could alternatively be provided on the bottom surface, without departing from the scope of the disclosure.

The cam surfaces 920 and the cam tracks 922 may each be complimentarily angled relative to a centerline 924 such that axial movement of the cam 918 in the proximal direction A relative to the jaw members 910a,b causes the jaw members 910a,b to open or otherwise separate laterally from each other. In contrast, axial movement of the cam 918 in the distal direction B relative to the jaw members 910a,b causes the jaw members 910a,b to close. The magnitude of the angled surfaces of the cam surfaces 920 and the cam tracks 922 relative to the centerline 924 will directly impact the opening and closing movement of the jaw members 910a,b. More specifically, a smaller (steeper) angle relative to the centerline 924 will cause the jaw members 910a,b to open or close more slowly as the cam 918 moves proximally or distally, respectively, relative to the jaw members 910a,b. In contrast, a larger (lower) angle relative to the centerline 924 will cause the jaw members 910a,b to open or close more quickly as the cam 918 moves proximally or distally, respectively, relative to the jaw members 910a,b. The angle of the surfaces of the cam surfaces 920 and the cam tracks 922 relative to the centerline 924 may range between about 10° and about 45°.

The opposing angled surfaces of the cam surfaces 920 and the cam tracks 922 may provide a lubricious interface to mitigate or eliminate friction between the cam 918 and the jaw members 910a,b. Any of the liquid-based or powder-based lubricants mentioned herein may be used, or otherwise, one or both of the angled surfaces 920, 922 may be polished to reduce or eliminate friction.

The actuation mechanism 916 may further include one or more biasing devices 926 (one shown) configured to continuously bias the jaws 904 toward the closed position. The biasing device 926 may be similar to the biasing devices 834 of FIGS. 8A-8C. While one biasing device 926 is depicted, more than one may be employed, without departing from the scope of the disclosure.

In the illustrated embodiment, the biasing device 926 acts on the cam 918 and provides a passive spring load that continuously urges the cam 918 distally relative to the jaw members 910a,b, which causes the cam surfaces 920 to slidably engage the cam tracks 922 and thereby urge the jaws 904 toward the closed position. In some embodiments, as illustrated, the biasing device 926 may interpose the cam 918 and a stop member 928 arranged proximal to the cam 918. The stop member 928 may be similar to the stop member 836 of FIGS. 8A-8C, and therefore will not be described again in detail.

To prevent the jaws 904 from closing or remaining at the closed position, the cam 918 may be selectively urged (pulled) in the proximal direction A, which causes the cam surfaces 920 to slidably engage the cam tracks 922 of the jaw members 910a,b and thereby urge the jaws 904 toward the open position. In some embodiments, one or more flexible members 930 (one shown as a dashed line) may be operatively coupled to the cam 918 and extend proximally to a drive housing (e.g., the drive housing 206 of FIG. 2). At the drive housing, the flexible member 930 may be operatively coupled to a drive input actuatable to urge (pull) the cam 918 in the proximal direction A and thereby maintain the cam 918 in proximal tension. The flexible member 930 may comprise, for example, a drive cable or a flexible shaft, which may prove advantageous in embodiments where the end effector 902 is arranged distal to an articulable wrist joint, and the flexible member 930 extends through the articulable wrist joint.

In other embodiments, however, the cam 918 may be operatively coupled to a rigid or semi rigid drive shaft (or rod) that extends from a drive housing (e.g., the drive housing 206 of FIG. 2). Alternatively, a portion of the cam 918 itself may instead extend to the drive housing. In such embodiments, the drive shaft (or the proximal end of the cam 918) may be operatively coupled to a drive input at the drive housing that urges the cam 918 in the proximal direction A and thereby maintains the cam 918 in proximal tension.

Example operation of the end effector 902 is now provided with continued reference to FIGS. 9A-9B. FIG. 9A shows the jaws 904 in the open position, and FIG. 9B depicts the jaws 904 after having been moved (actuated) to a closed position. In FIG. 9A, the surgical clip 906 may be received between the jaw members 910a,b when the jaws 904 are in the open position. Opening the jaws 904 may be accomplished by placing a tensile load on the cam 918 in the proximal direction A, and thereby causing the cam surfaces 920 to slidably engage the cam tracks 922 of the jaw members 910a,b. Moving the cam 918 in the proximal direction A builds up spring force in the biasing device 926 as engaged against the cam 918. The jaws 904 will be held in the open position as long as proximal tension (bias) is maintained on the cam 918.

In FIG. 9B, the surgical clip 906 has been crimped between the opposing jaw members 910a,b as the jaws 904 collapse toward each other during actuation. To move the jaws 904 to the closed position, and thereby crimp (crush) the surgical clip 906, proximal tension (biasing force) on the cam 918 may be released, which allows the spring force of the biasing device 926 to urge the cam 918 in the distal direction B relative to the jaws 904. Moving the cam 918 distally causes the cam surfaces 920 to slidably engage the cam tracks 922 of the jaw members 910a,b, and thereby urge the jaws 904 toward the closed position to crimp the surgical clip 906. Once the surgical clip 906 is crimped, proximal tension (bias) on the cam 918 may be initiated once more to move the jaw members 910a,b back to the open position in preparation for receiving another surgical clip.

Figure 10:
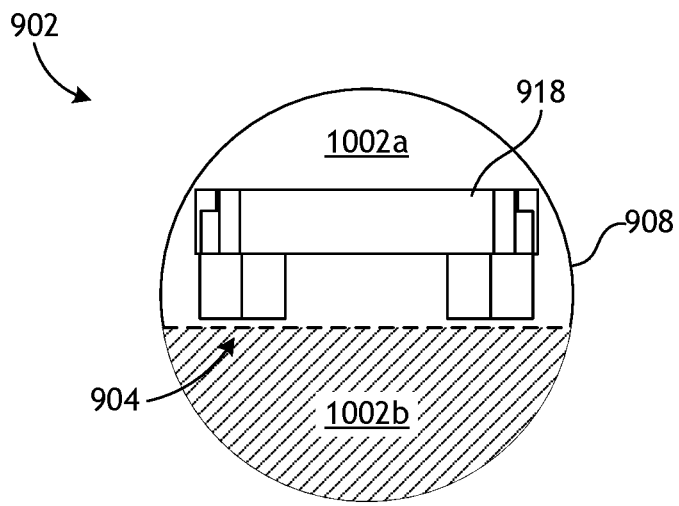
FIG. 10 is an end view of the end effector of FIGS. 9A-9B.

FIG. 10 is an end view of the end effector 902 of FIGS. 9A-9B. As illustrated, the housing 908 may be divided into a first hemisphere 1002a and a second hemisphere 1002b. The jaws 904 and the cam 918 may be generally positioned within the first hemisphere 1002a, which leaves the second hemisphere 1002b capable of accommodating other features or mechanisms of the end effector 902. For example, the second hemisphere 1002b may accommodate a clip loading mechanism and/or provide space for clip storage. Those skilled in the art will readily appreciate the advantage in minimizing the distal tip of any device, which increases access and visibility of a targeted structure. Internally to the device, additional components that are not shown require space to ensure clip feeding, and support to jaws.

Embodiments disclosed herein include:

A. An end effector for a surgical clip applier includes a housing, opposed first and second jaw members extending past a distal end of the housing and each comprising an independent structure movable relative to the other, a first cam track provided on the first jaw member and a second cam track provided on the second jaw member, a cam providing first and second cam surfaces slidably engageable with the first and second cam tracks, respectively, and a biasing device continuously urging the cam in a distal direction relative to the first and second jaw members, wherein the first and second cam surfaces and the first and second cam tracks are angled such that axial movement of the cam in the distal direction relative to the first and second jaw members causes the jaw members to close.

B. A surgical clip applier includes a drive housing, an elongate shaft that extends from the drive housing, and an end effector arranged at a distal end of the elongate shaft, the end effector including a housing, opposed first and second jaw members extending past a distal end of the housing and each comprising an independent structure movable relative to the other, a first cam track provided on the first jaw member and a second cam track provided on the second jaw member, a cam providing first and second cam surfaces slidably engageable with the first and second cam tracks, respectively, and a biasing device continuously urging the cam in a distal direction relative to the first and second jaw members, wherein the first and second cam surfaces and the first and second cam tracks are angled such that axial movement of the cam in the distal direction relative to the first and second jaw members causes the jaw members to close.

C. A method of operating a surgical clip applier includes positioning the surgical clip applier adjacent a patient for operation, the surgical clip applier including a drive housing, an elongate shaft extending from the drive housing, and an end effector arranged at a distal end of the elongate shaft, the end effector including a housing, opposed first and second jaw members extending past a distal end of the housing and each comprising an independent structure movable relative to the other, a first cam track provided on the first jaw member and a second cam track provided on the second jaw member, and a cam providing first and second cam surfaces slidably engageable with the first and second cam tracks, respectively. The method further includes continuously urging the cam in a distal direction relative to the first and second jaw members with a biasing device, axially moving the cam with the biasing device in the distal direction relative to the first and second jaw members and thereby closing the jaw members, wherein the first and second cam surfaces and the first and second cam tracks are angled such that axial movement of the cam in the distal direction closes the jaw members, and crimping a surgical clip disposed between the first and second jaw members as the jaw members close.

Each of embodiments A, B, and C may have one or more of the following additional elements in any combination: Element 1: wherein the cam comprises a lower cam, the first and second cam tracks comprise first and second lower cam tracks, respectively, and the first and second cam surfaces comprise first and second inner cam surfaces, respectively, the end effector further comprising a first upper cam track provided on the first jaw member and a second upper cam track provided on the second jaw member, and an upper cam that provides first and second outer cam surfaces slidably engageable with the first and second upper cam tracks, respectively. Element 2: wherein the upper cam is selectively movable in a proximal direction relative to the first and second jaw members, and wherein the first and second outer cam surfaces and the first and second upper cam tracks are angled such that axial movement of the cam in the proximal direction relative to the first and second jaw members causes the jaw members to open. Element 3: further comprising a flexible member operatively coupled to the upper cam and extending proximally therefrom, wherein proximal biasing force on the flexible member causes the jaw members to open. Element 4: wherein the first and second cam surfaces comprise angled slots defined in the cam and sized to receive the first and second cam tracks. Element 5: wherein the cam is selectively movable in a proximal direction relative to the first and second jaw members, and wherein the first and second cam surfaces and the first and second cam tracks are further angled such that axial movement of the cam in the proximal direction causes the jaw members to open. Element 6: further comprising a flexible member operatively coupled to the cam and extending proximally therefrom, wherein proximal biasing force on the flexible member causes the jaw members to open. Element 7: wherein the first jaw member defines a first inner surface and the second jaw member defines a second inner surface opposite the first inner surface, and wherein the first and second inner surfaces remain substantially parallel to each other as the jaw members open and close.

Element 8: further comprising an articulable wrist joint interposing the end effector and the elongate shaft. Element 9: wherein the cam comprises a lower cam, the first and second cam tracks comprise first and second lower cam tracks, respectively, and the first and second cam surfaces comprise first and second inner cam surfaces, respectively, the end effector further comprising a first upper cam track provided on the first jaw member and a second upper cam track provided on the second jaw member, and an upper cam that provides first and second outer cam surfaces slidably engageable with the first and second upper cam tracks, respectively. Element 10: wherein the upper cam is selectively movable in a proximal direction relative to the first and second jaw members, and wherein the first and second outer cam surfaces and the first and second upper cam tracks are angled such that axial movement of the cam in the proximal direction relative to the first and second jaw members causes the jaw members to open. Element 11: further comprising a flexible member operatively coupled to the upper cam and extending proximally therefrom, wherein proximal biasing force on the flexible member causes the jaw members to open. Element 12: wherein the first and second cam surfaces comprise angled slots defined in the cam and sized to receive the first and second cam tracks. Element 13: wherein the cam is selectively movable in a proximal direction relative to the first and second jaw members, and wherein the first and second cam surfaces and the first and second cam tracks are further angled such that axial movement of the cam in the proximal direction causes the jaw members to open. Element 14: further comprising a flexible member operatively coupled to the cam and extending proximally, wherein proximal biasing force on the flexible member causes the jaw members to open.

Element 15: wherein the cam comprises a lower cam, the first and second cam tracks comprise first and second lower cam tracks, respectively, and the first and second cam surfaces comprise first and second inner cam surfaces, respectively, the method further comprising placing a tensile load on an upper cam in a proximal direction and thereby opening the first and second jaw members, the upper cam providing first and second outer cam surfaces slidably engageable with first and second upper cam tracks provided on the first and second jaw members, respectively, and releasing the tensile load on the upper cam in the proximal direction and thereby allowing the first and second jaw members to close. Element 16: wherein the first and second cam surfaces comprise angled slots defined in the cam and sized to receive the first and second cam tracks, the method further comprising placing a tensile load on the cam in a proximal direction and thereby opening the first and second jaw members, wherein the first and second cam surfaces and the first and second cam tracks are further angled such that axial movement of the cam in the proximal direction causes the jaw members to open, and releasing the tensile load on the cam in the proximal direction and thereby allowing the first and second jaw members to close. Element 17: wherein the first jaw member provides a first inner surface and the second jaw member provides a second inner surface opposite the first inner surface, and wherein crimping a surgical clip disposed between the first and second jaw members further comprises moving the first and second jaw members from an open position to a closed position, and maintaining the first and second inner surfaces substantially parallel to each other as the first and second jaw members move to the closed position.

By way of non-limiting example, exemplary combinations applicable to A, B, and C include: Element 1 with Element 2; Element 2 with Element 3; Element 4 with Element 5; Element 5 with Element 6; Element 9 with Element 10; Element 10 with Element 11; Element 12 with Element 13; and Element 13 with Element 14.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An end effector for a surgical clip applier, comprising:
   a housing;
   opposed first and second jaw members extending past a distal end of the housing, each jaw member having opposing first and second free ends and comprising separate and independent structures movable relative to the other;
   a first cam track provided on the first jaw member and a second cam track provided on the second jaw member;
   a cam providing first and second cam surfaces slidably engageable with the first and second cam tracks, respectively, wherein the first and second cam surfaces and the first and second cam tracks are angled such that distal movement of the cam closes the jaw members; and
   a biasing device continuously urging the cam distally to bias the first and second jaw members toward a closed position.

2. The end effector of claim 1, wherein the cam comprises a lower cam, the first and second cam tracks comprise first and second lower cam tracks, respectively, and the first and second cam surfaces comprise first and second inner cam surfaces, respectively, the end effector further comprising:
   a first upper cam track provided on the first jaw member and a second upper cam track provided on the second jaw member; and
   an upper cam that provides first and second outer cam surfaces slidably engageable with the first and second upper cam tracks, respectively.

3. The end effector of claim 2, wherein the upper cam is selectively movable in a proximal direction relative to the first and second jaw members, and wherein the first and second outer cam surfaces and the first and second upper cam tracks are angled such that axial movement of the cam in the proximal direction relative to the first and second jaw members causes the jaw members to open.

4. The end effector of claim 3, further comprising a flexible member operatively coupled to the upper cam and extending proximally therefrom, wherein proximal biasing force on the flexible member causes the jaw members to open.

5. The end effector of claim 1, wherein the first and second cam surfaces comprise angled slots defined in the cam and sized to receive the first and second cam tracks.

6. The end effector of claim 5, wherein the cam is selectively movable in a proximal direction relative to the first and second jaw members, and wherein the first and second cam surfaces and the first and second cam tracks are further angled such that axial movement of the cam in the proximal direction causes the jaw members to open.

7. The end effector of claim 6, further comprising a flexible member operatively coupled to the cam and extending proximally therefrom, wherein proximal biasing force on the flexible member causes the jaw members to open.

8. The end effector of claim 1, wherein the first jaw member defines a first inner surface and the second jaw member defines a second inner surface opposite the first inner surface, and wherein the first and second inner surfaces remain substantially parallel to each other as the jaw members open and close.

9. A surgical clip applier, comprising:
   a drive housing;
   an elongate shaft that extends from the drive housing; and
   an end effector arranged at a distal end of the elongate shaft, the end effector including:
      opposed first and second jaw members extending past a distal end of a housing, each jaw member having opposing first and second free ends and comprising separate and independent structures movable relative to the other;

a first cam track provided on the first jaw member and a second cam track provided on the second jaw member;

a cam providing first and second cam surfaces slidably engageable with the first and second cam tracks, respectively, wherein the first and second cam surfaces and the first and second cam tracks are angled such that distal movement of the cam closes the jaw members; and a biasing device continuously urging the cam distally to bias the first and second jaw members toward a closed position.

10. The surgical clip applier of claim 9, further comprising an articulable wrist joint interposing the end effector and the elongate shaft.

11. The surgical clip applier of claim 9, wherein the cam comprises a lower cam, the first and second cam tracks comprise first and second lower cam tracks, respectively, and the first and second cam surfaces comprise first and second inner cam surfaces, respectively, the end effector further comprising:

a first upper cam track provided on the first jaw member and a second upper cam track provided on the second jaw member; and an upper cam that provides first and second outer cam surfaces slidably engageable with the first and second upper cam tracks, respectively.

12. The surgical clip applier of claim 11, wherein the upper cam is selectively movable in a proximal direction relative to the first and second jaw members, and wherein the first and second outer cam surfaces and the first and second upper cam tracks are angled such that axial movement of the cam in the proximal direction relative to the first and second jaw members causes the jaw members to open.

13. The surgical clip applier of claim 12, further comprising a flexible member operatively coupled to the upper cam and extending proximally therefrom, wherein proximal biasing force on the flexible member causes the jaw members to open.

14. The surgical clip applier of claim 9, wherein the first and second cam surfaces comprise angled slots defined in the cam and sized to receive the first and second cam tracks.

15. The surgical clip applier of claim 14, wherein the cam is selectively movable in a proximal direction relative to the first and second jaw members, and wherein the first and second cam surfaces and the first and second cam tracks are further angled such that axial movement of the cam in the proximal direction causes the jaw members to open.

16. The surgical clip applier of claim 15, further comprising a flexible member operatively coupled to the cam and extending proximally, wherein proximal biasing force on the flexible member causes the jaw members to open.

17. A method of operating a surgical clip applier, comprising:

positioning the surgical clip applier adjacent a patient for operation, the surgical clip applier including a drive housing, an elongate shaft extending from the drive housing, and an end effector arranged at a distal end of the elongate shaft, the end effector including:

opposed first and second jaw members extending past a distal end of a housing, each jaw member having opposing first and second free ends and comprising separate and independent structures movable relative to the other;

a first cam track provided on the first jaw member and a second cam track provided on the second jaw member; and a cam providing first and second cam surfaces slidably engageable with the first and second cam tracks, respectively, wherein the first and second cam surfaces and the first and second cam tracks are angled such that distal movement of the cam closes the jaw members;

continuously urging the cam distally with a biasing device;

moving the cam distally with the biasing device and thereby closing the jaw members; and crimping a surgical clip disposed between the first and second jaw members as the jaw members close.

18. The method of claim 17, wherein the cam comprises a lower cam, the first and second cam tracks comprise first and second lower cam tracks, respectively, and the first and second cam surfaces comprise first and second inner cam surfaces, respectively, the method further comprising:

placing a tensile load on an upper cam in a proximal direction and thereby opening the first and second jaw members, the upper cam providing first and second outer cam surfaces slidably engageable with first and second upper cam tracks provided on the first and second jaw members, respectively; and releasing the tensile load on the upper cam in the proximal direction and thereby allowing the first and second jaw members to close.

19. The method of claim 17, wherein the first and second cam surfaces comprise angled slots defined in the cam and sized to receive the first and second cam tracks, the method further comprising:

placing a tensile load on the cam in a proximal direction and thereby opening the first and second jaw members, wherein the first and second cam surfaces and the first and second cam tracks are further angled such that axial movement of the cam in the proximal direction causes the jaw members to open; and releasing the tensile load on the cam in the proximal direction and thereby allowing the first and second jaw members to close.

20. The method of claim 17, wherein the first jaw member provides a first inner surface and the second jaw member provides a second inner surface opposite the first inner surface, and wherein crimping a surgical clip disposed between the first and second jaw members further comprises:

moving the first and second jaw members from an open position to a closed position; and maintaining the first and second inner surfaces substantially parallel to each other as the first and second jaw members move to the closed position.

* * * * *